United States Patent
Müller et al.

(10) Patent No.: US 9,387,052 B2
(45) Date of Patent: Jul. 12, 2016

(54) APPLICATION DEVICE

(75) Inventors: Frank Müller, Feldkrich (AT); Klaus Galehr, Schlins (AT); Sebastian Holaschke, Bregenz (AT); Ralf Suffel, Haag (CH)

(73) Assignee: Ivoclar Vivadent AG, Schaan (LI)

( * ) Notice: Subject to any disclaimer, the term of this patent is extended or adjusted under 35 U.S.C. 154(b) by 173 days.

(21) Appl. No.: 12/943,351

(22) Filed: Nov. 10, 2010

(65) Prior Publication Data

US 2011/0137262 A1    Jun. 9, 2011

(30) Foreign Application Priority Data

Dec. 4, 2009  (EP) .................................... 09178109
Apr. 9, 2010  (EP) .................................... 10159504

(51) Int. Cl.
*A61M 5/315* (2006.01)
*A61M 5/31* (2006.01)
*A61C 5/06* (2006.01)

(52) U.S. Cl.
CPC ............ *A61C 5/062* (2013.01); *A61M 5/31511* (2013.01); *A61M 5/31513* (2013.01); *A61M 5/31515* (2013.01); *A61M 2005/3103* (2013.01); *A61M 2005/3123* (2013.01)

(58) Field of Classification Search
CPC ..................... A61M 5/31511; A61M 5/31513; A61M 5/31515; A61M 2005/31521; A61M 2005/3123; A61M 2005/3103; A61C 5/062
USPC ......... 604/141, 142, 146, 152, 153, 213, 217, 604/222, 128, 129
See application file for complete search history.

(56) References Cited

U.S. PATENT DOCUMENTS

| | | | | |
|---|---|---|---|---|
| 3,834,387 A | * | 9/1974 | Brown .......................... | 604/125 |
| 5,411,488 A | * | 5/1995 | Pagay ................ | A61M 5/31513 604/218 |
| 5,620,423 A | * | 4/1997 | Eykmann ................ | A61C 5/062 604/218 |
| 6,582,399 B1 | * | 6/2003 | Smith et al. .................... | 604/152 |
| 6,796,217 B2 | * | 9/2004 | Horita et al. .................... | 92/240 |
| 6,835,191 B2 | * | 12/2004 | Lee ...................... | A61M 5/1782 604/228 |
| 2005/0182371 A1 | * | 8/2005 | Wagner ................. | A61M 5/007 604/218 |

* cited by examiner

*Primary Examiner* — Emily Schmidt
*Assistant Examiner* — Lauren M Peng
(74) *Attorney, Agent, or Firm* — Ann M. Knab; Thad McMurray

(57) ABSTRACT

An application device with a cylindrical basic body for storing a squeezable dental material having a piston positioned inside the basic body and axially displaceable towards the basic body. A piston rod serves to displace the piston in the squeezing direction, which piston rod partially reaches into the piston and is axially displaceable towards the latter. The piston is provided with an elastic resetting device at its front end area positioned in the direction towards the dental material. The elastic resetting device can be biased in the squeezing direction, and returns back to its relaxed position after the end of each axial movement of the piston in the squeezing direction and release of the pressure exerted on the piston rod for this purpose.

13 Claims, 5 Drawing Sheets

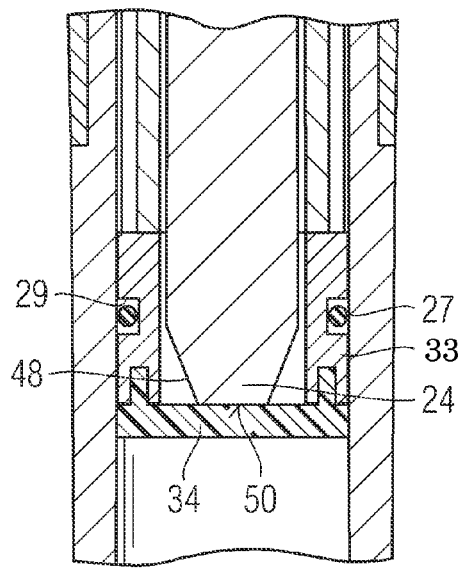 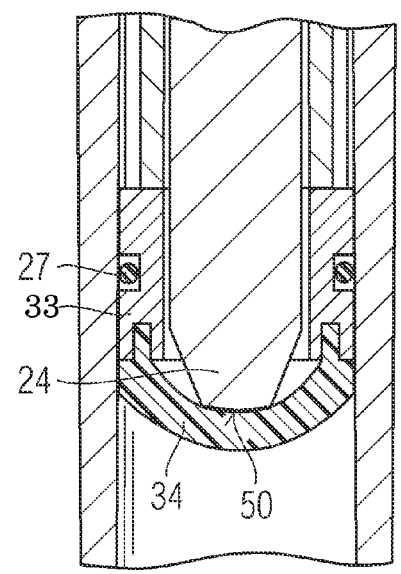
Fig. 5                    Fig. 6

APPLICATION DEVICE

CROSS-REFERENCE TO RELATED APPLICATIONS

This application claims the benefit of European Patent Application Serial No. 09178109.6 filed Dec. 4, 2009 and European Patent Application Serial No. 10159504.9, filed Apr. 9, 2010, which are hereby incorporated by reference in their entirety.

TECHNICAL FIELD

The present invention relates generally to an application device for dispensing dental material and in particular to application devices having controlled discharge of dental materials.

BACKGROUND

An example of an application device for dental materials is found in U.S. Pat. No. 5,620,423, which is hereby incorporated by reference. This device includes a plug which has an elastic diaphragm surface. A rotary piston presses the diaphragm surface, and together with the plug, in the direction of an exit nozzle, the material to be squeezed out is put under pressure. This condition of being under pressure is thought to be unfavourable for storage, and therefore in the solution mentioned, the rotary piston is supposed to be rotated in such a fashion that the pressure is released from the material once the squeezing action is finished. Such rotary pistons are considered to be necessary whenever viscous dental materials are to be squeezed out without any particular squeezing device being inserted in the cartridge. In practice, however, the return to stable position is not regularly achieved and/or the rotary piston is sometimes turned in the squeezing direction if the operator does not regularly employ the cartridge concerned.

With viscous, medium viscous and slightly viscous dental materials, problems can arise due to a certain elasticity of the material and also due to a certain "plastic-flow persistence" or incomplete wiping-off, where some dental material may be present outside the tip of the cartridge, which is easily contaminated. Although this material can be wiped off if the device is operated in a careful fashion, in practice, this is not always performed, and thus, this solution is not generally accepted.

Different attempts have been made to overcome the disadvantages of known cartridges. For instance, it has been suggested to provide a special deformation body inside a cartridge upon which shearing forces are exerted and which exerts a resetting impulse. However, dripping of excess material is not prevented with this body in many cases because the shearing deformation is possible only to a very low extent, such that if real drops form, these may drip off if, in particular, materials of a lower viscosity are used.

In order to remedy this problem, it has been suggested to provide a friction guide for the diaphragm by increasing the friction between a diaphragm element and the cartridge wall. For this purpose, the diaphragm element is supported at the actual piston with a predetermined clearance, with the piston extending to the wall of the cartridge, in order to provide possible guidance, even though the diaphragm element has no stability of its own.

In this solution, the diaphragm element has a flange extending to the rear and working with the help of a shoulder pointing inwards against a corresponding shape of the piston rod, such that the clearance can be guided in the desired fashion.

By actuating the piston towards the front, the diaphragm element is centrally deformed and is buckled to the front. This deformation, however, is very disadvantageous for the contact with the outer surface, i.e. the contact between the diaphragm element and the cartridge. As a result, the diaphragm element is virtually pulled inside, such that foreign substances, e.g., the dental material to be squeezed out, may easily flow into the clearance between the diaphragm element and the wall, destroying the desired sealing effect.

Although the rear area of the diaphragm element may still be in contact at first, it is not supported by the piston rod, and the virtually wedge-shaped extension of the dental material taken up and being positioned in the margin will be moved towards the rear when the dental material is squeezed out, such that the desired sealing effect is not achieved, which may easily result in the diaphragm element getting stuck or even being destroyed.

It is basically known to seal a piston via a cartridge with a sealing, such as an o-ring sealing, for instance. Here, care must always be taken to prevent any contamination from reducing the sealing function itself, in particular if greater pressures are exerted.

SUMMARY

Embodiments of the invention provide an application device for dispensing of both fluid and viscous dental materials. The application device includes a cylindrical body for storing a squeezable dental material, a piston positioned inside the cylindrical body and axially displaceable towards the cylindrical body, and a piston rod serving to displace the piston in a squeezing direction, wherein the piston rod extends into the piston and is axially displaceable towards the piston. An elastic resetting device is disposed at a front end area of the piston and positioned in the direction towards the dental material, wherein the elastic resetting device is adaptable to be biased in the squeezing direction and to return back to a relaxed position after the end of each axial movement of the piston in the squeezing direction and at the release of the pressure exerted on the piston rod for this purpose. Accordingly, dripping of excess dental material from the application device is prevented by creating a partial vacuum inside the cylindrical body, with the elastic resetting device pressing the piston rod in a direction opposite the squeezing direction. A stop disposed on the piston rod and facing the squeezing direction, is positioned at a spatial distance from the resetting device, wherein the bias in the resetting device is limited by the stop on the piston rod when the piston rod is actuated in the squeezing direction.

In an embodiment of the present invention, the application device is intended to safely guide a special case-shaped piston which is flatly supported at its inside. This ensures that even if a tension force is applied by the piston rod to the central area of an elastic resetting element of the piston, it does not contract radially in its circumferential area, but only slides axially, in such a fashion that dental material is permitted to enter in this position. The predetermined stop which is positioned at a spatial distance from the resetting device guarantees a defined relative movement between the piston rod and the piston. It is particularly advantageous for the stop and the counter-stop to be made out of comparably hard materials which guarantee a secure forward drive even with highly viscous material, without excessive load being exerted on the rather soft elastic resetting element. A large-area support of the elastic resetting element with the help of the piston can therefore be guaranteed and excessive load on diaphragm-like elements can be safely prevented.

In a further embodiment of the present invention, the elastic resetting element can be deformed independently of the contact of the piston with the basic body of the application device, i.e. the cartridge body. In particular, the curved biased part or diaphragm dome of the elastic resetting element resulting from the piston rod tip entering there does not pull the piston element inwards, such that the sealing positioned there inside a circular groove pointing outwards provides a secure sealing effect against the basic body.

In another embodiment of the present invention, the mere sealing function is separated from the deformation function, which is particularly favorable since the materials used can be optimized, respectively, without taking into consideration the respective other function.

In yet further embodiments of the present invention, a rather hard and rigid plastic material can be selected to form a piston body of the piston. In contrast to this, the elastic resetting element is clearly softer and elastically deformable. The elastic resetting element can preferably be formed as the front portion of the piston, and the piston body preferably extends over the front portion of the length of the piston rod, for example over the front 20%, such that a safe and low-friction guidance is also guaranteed.

In a preferred embodiment, the relative movement between the piston rod and piston is preferably visible from the exterior. The dentist or dental technician who employs the application device in accordance with an embodiment of the present invention can in this way realize virtually automatically that the piston rod may be further inserted into the piston by means of pressure exerted on the actuation element, such that the diaphragm dome is virtually visible from the exterior. For this purpose, the piston can either be prolonged or extended over the rear area of the piston rod, or the piston movement can be made visible with the help of a slot-shaped window in the basic body.

In a further embodiment, it is virtually automatically guaranteed by removing the pressure on the piston rod, that the pressure on the dental material in the inner space of the application device is removed, such that the dental technician can then safely remove the application device from the place of application without having to worry that excess dental material may drip out.

In still a further embodiment, with the help of the combination of a diaphragm and significant resetting forces which are larger than the frictional forces of a piston rod, a defect-free, simple cartridge or application device which yet prevents the dripping out of excess material is surprisingly provided. By realizing the case-shaped piston, a secure guidance over the entire length of the application device can be guaranteed, and a comparably large guiding surface is provided which squeezes the dental material towards the front and presses the freely elastic resetting diaphragm into the right direction as a resetting element at the front side of the piston rod. It is particularly favorable in this context for the case-shaped piston to be taken over the diaphragm by the piston rod for the purpose of squeezing out the dental material, at the same time, however, to provide a larger friction against the inner wall of the basic body than the friction between the piston rod and the piston. This ensures that when the resetting device springs back, the piston rod is moved since it is easily displaceable inside the piston.

In a further aspect, this feature may be guaranteed in particular with the help of three symmetrically spread ribs which extend with a small contact surface, for instance spherically, towards the piston rod and protrude radially inwards from the piston. It is to be understood that instead, a kinematic exchange may also be undertaken such that ribs extend from the piston rod towards the piston.

In accordance with another embodiment, it is particularly favorable for the piston rod to have an essentially planar front surface which flatly supports the resetting element, for instance in the central area. This embodiment has the particular advantage that the resetting element is able to flatly extend during the forward drive, in which condition the largest pressure is exerted on the resetting element, and it is not stretched. The extension of the central front surface may either be over almost the entire free area, except a small clearance at the margin, towards the piston, or may amount to, for example, about half the diameter of the resetting element. At the end area of the front surface, a chamfer is preferably provided, or even more preferably a radius, which makes a smooth redirection of the resetting element possible whenever the driving force of the piston rod meets such great resistance that the piston is slightly pressed back relative to the front surface of the piston rod.

It is in any case preferred for the free front surface of the resetting element, i.e. the surface facing towards the dental material, to extend in such a fashion as to prevent any undercut, with the possibility of providing a concave or a convex or a plane driving front surface in the relaxed state, depending on the requirements of the dental material to be squeezed out.

In a preferred embodiment of the application device, it is intended that the resetting force of the resetting element is larger than the deformation friction of the dental material. As a result, the dental material is drawn back even if it is highly viscous, and the dripping out of excess material is safely prevented.

In another preferred embodiment, it is intended that the elastic resetting element is provided with a larger thickness on the wall at the central area. The larger thickness of the wall makes it possible to uniformly spread the pressure arising as a result of the compression. In this context, it is particularly advantageous for the thicker wall area to have a trapezoid cross section, for this further improves the introduction of the force such that the pressure exerted by the piston rod by its front surface is even better spread to the resetting element in a uniform fashion. The resetting element is preferably essentially bonnet or pot shaped, with the wall having smaller constant thickness in the cylindrical area. The surrounding central area is particularly elastic, such that the desired elasticity can be guaranteed without any problems, and in particular without any peak stresses occurring in the material, which might lead to the elastic resetting element getting torn.

The connection can be provided in a frictional and/or positive fashion and may be adapted to the requirements to a large extent.

The piston rod may have a shape in the area of its piston rod tip which permits the deformation of the diaphragm by a rather large volume without exerting too much punctual stress on the diaphragm. The piston rod can be shaped in the form of a push rod and become slightly tapered towards the front, but it is in no way limited to this shape. It can have an essentially flat front surface which may end with a radius or a chamfer against the taper.

In a preferred embodiment, the resetting element is plane or planar at its front surface in the unloaded state, such that it can be in contact with the also plane or planar front surface of the piston rod. In an alternative embodiment, it is concave in the unloaded state, i.e. domed towards the piston rod. In this embodiment, the piston rod tip may also be plane or planar, and there is the possibility for the diaphragm to buckle forward through the "zero position", i.e. the planar position, in order to squeeze out the dental material, which almost doubles the stroke of the diaphragm.

In a preferred embodiment, the piston body further has an outward circular peripheral groove which supports a sealing ring. The peripheral sealing guarantees a liquid-tight sealing, whereas the comparably hard piston element ensures that when viscous dental materials are used, they cannot enter into the clearance between the piston element and the basic body.

In yet another preferred embodiment, it is intended that in the relaxed position of the resetting device, the piston rod is in contact with a contact surface of the resetting device pointing opposite the squeezing direction, and the stop of the piston rod is positioned at a distance from the respective counter-stop of the piston corresponding to the function of the maximum bias of the resetting device.

In a further preferred embodiment, it is intended that in particular the contact area of the resetting element can be biased when a squeezing force is applied by the piston rod acting in the squeezing direction.

In still another preferred embodiment, it is intended that the wall of the resetting device is greater in thickness in the contact area with respect to the remaining wall of the resetting device.

In another preferred embodiment, it is intended that the elastic resetting device is firmly connected with a tapered outer circumference of the piston.

In yet another preferred embodiment, the piston and the piston rod are mounted threadlessly translatory relative to each other and threadlessly axially displaceable relative to the basic body, and the driving force of the piston relative to the basic body is larger than the resisting force of the elastic resetting device against deformation.

In still another preferred embodiment, it is intended that at the outer circumference of the piston at least two sealing ribs are formed surrounding the circumference, which sealing ribs act against the basic body, and at the piston rod and/or at the piston, a peripheral mounting groove or a mounting shoulder is formed for mounting a sealing ring made out of an elastic material.

In a further preferred embodiment, it is intended that the piston rod extends through the piston to the contact area of the resetting device, and the stop between the piston rod and the piston is formed in the elongation of the piston, preferably, approximately at its axial center.

In one more preferred embodiment, it is intended that the piston has at least one sliding rib at its rear end, sat which rib it is supported at the piston rod in a low-friction fashion.

In a further preferred embodiment, it is intended that the application device has an application nozzle which is attached to a surface of the basic body pointing in the squeezing direction.

In yet a further preferred embodiment, it is intended that the basic body is fillable with the application nozzle removed, and the piston and the piston rod are pressed back during the filling process.

In at least one more embodiment, it is intended that the piston rod has at least one peripheral groove which serves to mount a seal that is in contact with the inner walls of the basic body in such a fashion that it has a sealing function.

BRIEF DESCRIPTION OF THE DRAWINGS

Embodiments of the present invention will be more fully understood and appreciated by the following Detailed Description in conjunction with the accompanying drawings, in which:

FIG. 5 is an enlarged depiction of the front end of the piston rod and the surrounding areas of the application device in FIG. 3.

FIG. 6 is an enlarged depiction of the front end of the piston rod and the surrounding areas of the application device in FIG. 4.

DETAILED DESCRIPTION

Figure 1:
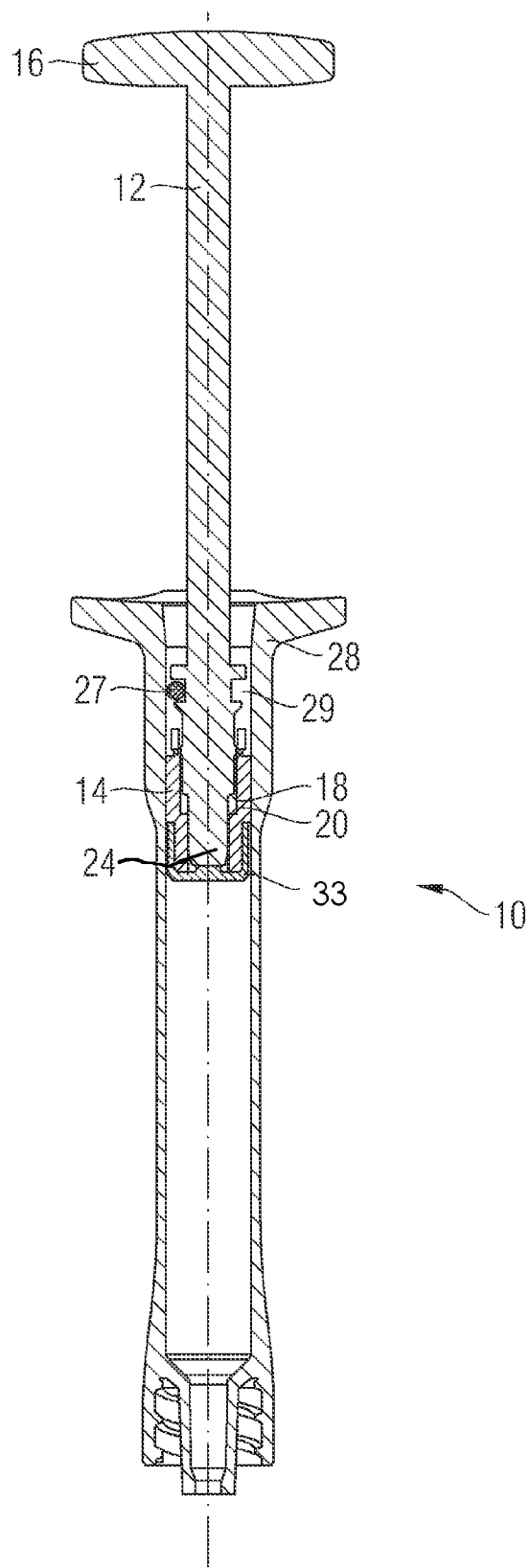
FIG. 1 is a cross-sectional view of an embodiment of an application device in accordance with the present invention, with the piston and the piston rod in the drawn-back position.

Reference is made to FIG. 1, which shows an application device 10 having a piston rod 12 and a piston 14. The piston rod 12 is guided inside the piston 14 in an axially moveable fashion. The piston rod 12 includes an actuation element 16 at its rear end, which element is shaped in accordance with a type of a handle of a syringe plunger. Actuating element 16 assists in pressing the piston rod 12 and the piston 14 forward.

For this purpose, the piston rod 12 has a stop 18 which acts on a counter-stop 20 of the piston 14. The piston rod 12 ends at its front end, in a piston rod tip 24. At this same end, the piston 14 ends in an elastic resetting element 33, which is firmly connected with a piston body 25 at which the counter-stop 20 is positioned. The elastic resetting element 33 is described in more detail as part of a resetting device for the piston rod 12 with reference to FIG. 2.

Figure 2:
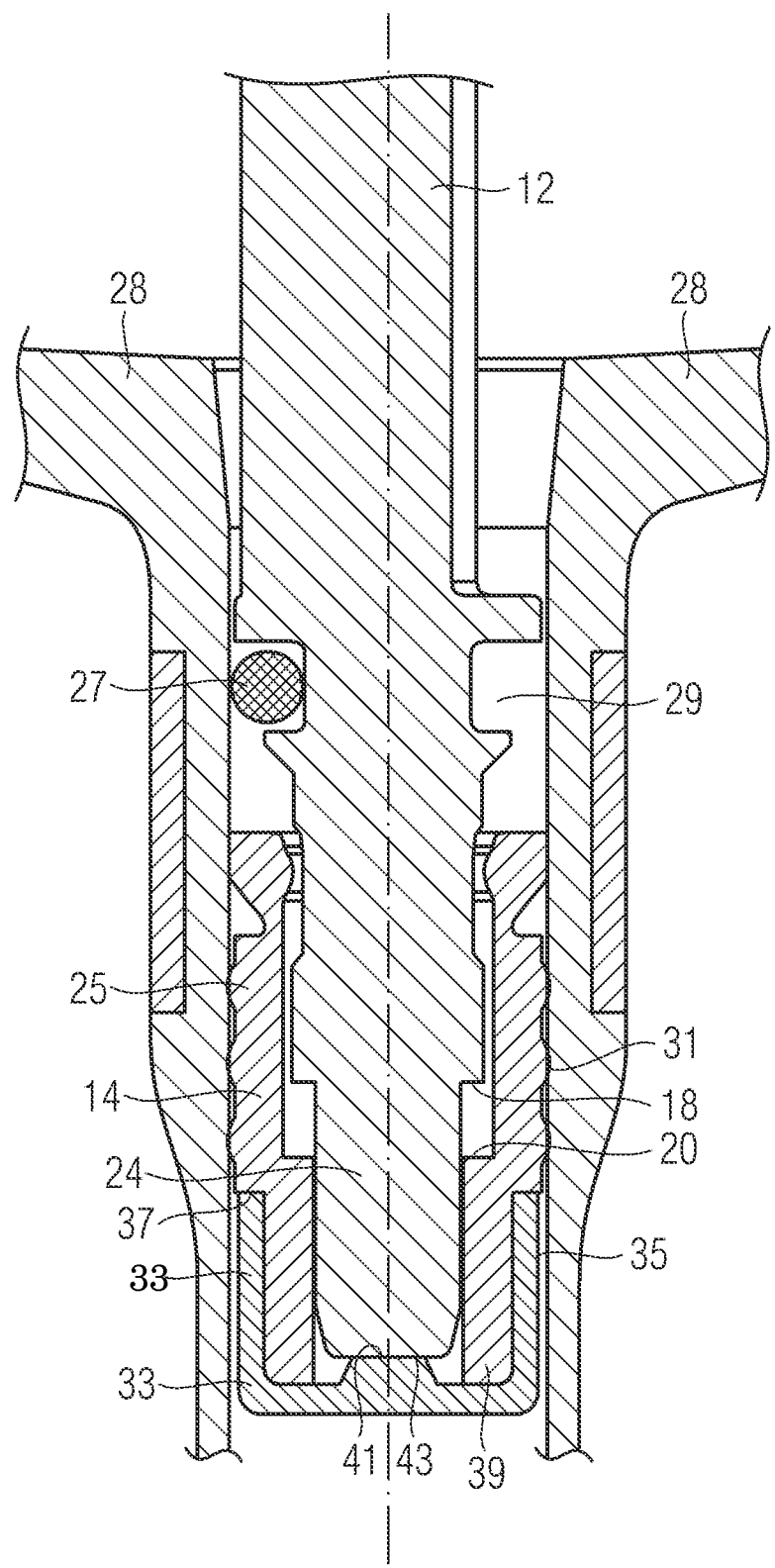
FIG. 2 is an enlarged depiction of a detail of the application device in FIG. 1.

FIG. 2 shows the piston body 25 with peripheral ribs 31, which act as a sealing means against a basic body 28. In addition, a circular groove 29 is provided into which an o-ring 27 may be inserted if necessary.

It can be seen from FIG. 2 how the piston rod 12 extends into the piston 14 with its piston rod tip 24. The structure of the piston 14 is also visible in detail. As already stated, the piston consists of a piston body 25 and an elastic resetting element 33. In the mounting position of the piston body 25, the elastic resetting element 33 forms the elastic resetting device. For this purpose, the elastic resetting element 33, which consists of a softer and more elastic material than the piston body 25, has an essentially bonnet- or pot-shaped structure and encloses the piston body 25. A cylindrical area 35 ends at the front surface in a shoulder 37 of the piston body 25. At this point, a connection between the elastic resetting element 33 and the piston body 25 is intended, either by means of gluing or in any other suitable fashion, with it being possible also to produce the two parts 25 and 33 as one piece, particularly preferably by means of injection molding using similar or different materials.

The piston body 25 has a tube-shaped section 39 which at its outer surface guides the cylindrical area 35 within the plane of the elastic resetting element 33. This makes possible an axial movement between the elastic resetting element 33 and the piston body 25 when the elastic resetting element 33 is stretched.

The pot- or bonnet-shaped elastic resetting element 33 has constant wall thickness everywhere except at contact area 41. The contact area 41 is shaped more thickly, positioned in the direction towards the piston rod tip 24, and contacting the front end area, i.e. the piston rod tip 24 of the piston rod 12, at the front surface 43.

The contact area 41 of the elastic resetting element 33 extends in a radial direction over less than half the diameter of the elastic resetting element 33, preferably over about only ⅓ of its diameter. Thus, a particularly favorable contact with low friction is realized, which facilitates a buckling of the elastic resetting element 33 in the direction towards the dental material. The biasing of the elastic resetting element or dome is limited by the stop 18 and the counter-stop 20 at the piston body 25 and the piston rod 12, respectively, with the extension of the dome being limited by the distance between those in the relaxed position of the piston rod 12.

In the elastic resetting element 33, the force introduced via the contact area 41 is introduced into the elastic resetting element 33 in a particularly favorable fashion. Accordingly, the contact area 41 has an essentially trapezoidal cross section, with the shorter side of the trapezoid at the front side 43 and the longer side of the trapezoid in the direction towards the elastic resetting element 33. The forces introduced are thus spread over a large area, although there is a relatively small contact surface between the elastic resetting element 33 and the piston rod tip 24.

Due to the sliding area provided between the cylindrical area 35 and the tube-shaped portion 39, a rather large length of extension is available, which is further favorable for the distribution of force of the pressure introduced via the piston rod 12.

It is particularly favorable that the piston rod 12 springs back automatically and thus takes in dental material automatically when the force on it is removed. For this purpose, it is intended that the friction at the ribs 31 between the piston 14 and the basic body 28 is larger than the spring force which the elastic resetting element 33 exerts on the piston rod tip 24, and this is the case until the stop 18 reaches the counter-stop 20. Only when this stable contact is reached, does the piston 14 begin to move together with the piston rod 12, and when it has reached its target position, the piston rod 12 springs back automatically.

The relative movement between the piston rod and the piston is preferably visible from the outside, and this is the case even if the piston rod 12 and the piston 14 are pressed entirely into the application device. Instead of the combination of the element 16 with the stop 20 realized here, the relative position between piston and piston rod can also be made visible with the help of a window in the basic body 28.

Figure 3:
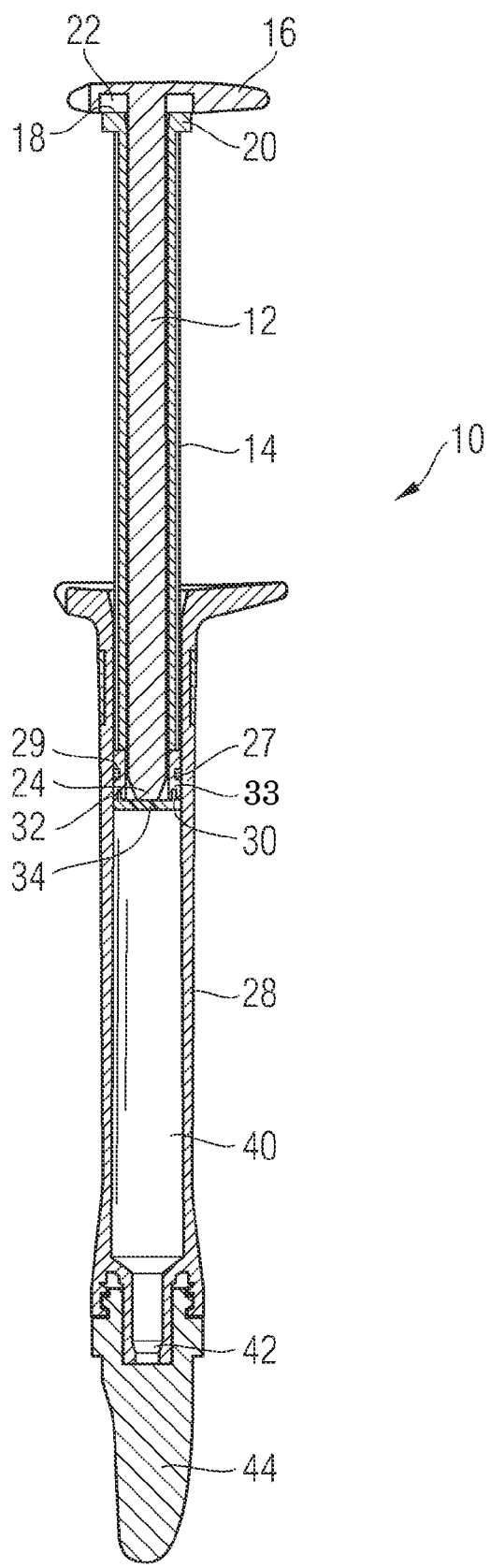
FIG. 3 is a cross-sectional view of an embodiment of an application device in accordance with the present invention, with the piston rod and the piston being drawn back.

Reference is made to FIG. 3, in which an embodiment of an application device in accordance with the present invention is shown. In this embodiment, the piston 14 extends over essentially the entire length of the piston rod 12, and the stop 18 is formed in the rear area of an actuation element 16, which has a ring-shaped recess 22 suitable for this purpose, into which the piston 14 may enter with its counter-stop 20.

An elastic resetting element 33 is provided, which is merely exerted by the pressure of the piston rod 12 in a central area, and which is deformed, with the frictional forces between the piston 14 and the basic body 28 being larger than the frictional forces between the piston rod 12 and the piston 14 plus the resetting forces of the elastic resetting element 33 here as well.

When the piston rod tip 24 and the elastic resetting element 33 are in a relative position to each other in which both end at the same position towards the front, the pressure body itself has not yet entered the recess 22 of the actuation element 16; the distance until reaching the stop 18 corresponds to about half the diameter of the piston rod 12.

In the elastic resetting element 33, a frontal groove 30 is formed over the front surface which takes up a circular flange 32 of a diaphragm 34.

The diaphragm 34 is formed elastically and has a thickness of clearly less than half the diameter of the piston rod 12, for instance ¹⁄₁₀ to ⅓, and in particular about ⅕, of the diameter.

The diaphragm 34 is elastic, and in the state depicted in FIG. 3, in which the piston rod tip 24 and the diaphragm 34 extend flatly to each other, the piston rod tip 24 is in contact with the diaphragm 34, but without deforming it.

In the inside space 40 of the pressure body 28, dental material is taken up in front of the diaphragm 34, which dental material can be squeezed out of the application device 10 via a nozzle 42. In the state depicted in FIG. 3, the nozzle 42 is closed with a cap 44 in a basically known fashion, in order to prevent the dental material in the inside space from drying out.

Figure 4:
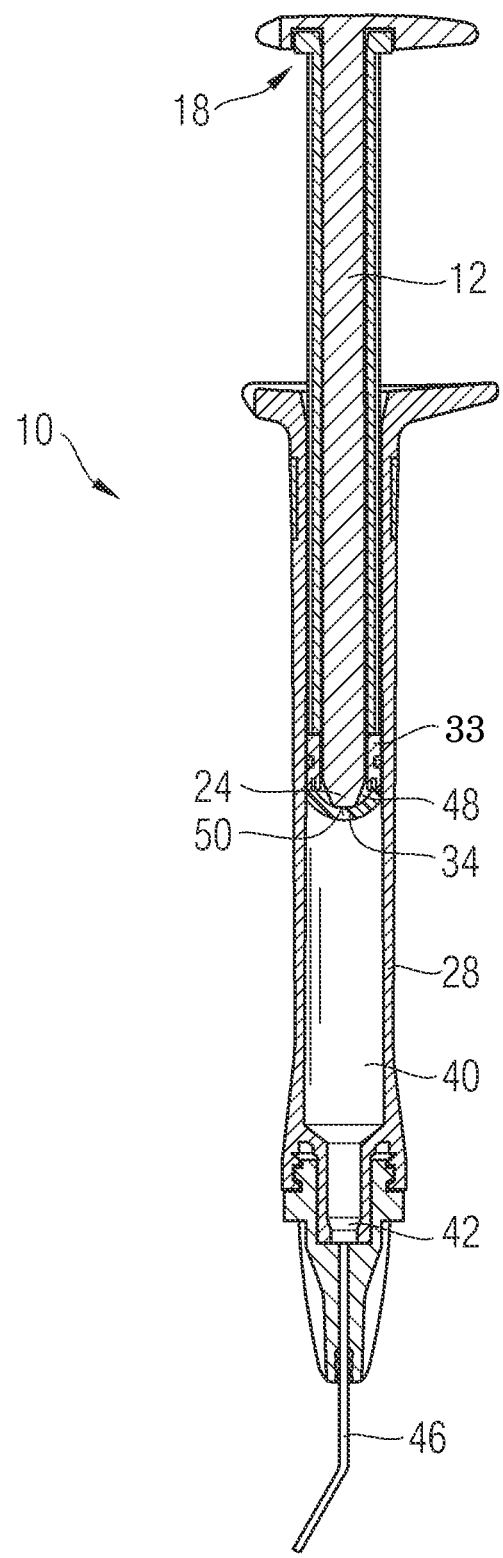
FIG. 4 is a cross-sectional view of the application device in FIG. 3, with the piston rod being pressed forward for the purpose of squeezing out the dental material.

FIG. 4 depicts in what fashion the dental material is squeezed out of the application device 10. For the purpose of applying the dental material, an extrusion element 46 is placed on the nozzle 42, with the design of the extrusion element being adaptable to the requirements to a large extent. If, for instance, a root treatment of a tooth is to be carried out, an extrusion element with a needle-shaped end having a hollow channel, which is suitable for this purpose, is applied.

The extrusion element 46 has a predetermined flow resistance which is to a large extent dependent on the viscosity of the dental material inside the basic body 28. In accordance with the present invention, it is possible to apply rather fluid dental material via an extrusion element with a narrow flow aperture as well as viscous dental material via the nozzle 42 or an extrusion element with a respectively large diameter, or even liquid dental material through a comparatively large diameter. The application device in accordance with the present invention offers a large range of possibilities for employment with different application situations and dental materials.

In accordance with the present invention, it is intended to have the diaphragm 34 buckle forward through the piston rod 12 opposite the elastic resetting element 33 for this purpose, with this dome reaching forward to the stop 18 between the element 16 and the piston rod 12.

The diaphragm 34 is pressed forward by the piston rod tip 24, such that it is buckled forward in the shape of a dome into the direction of the dental material. In this context, it is particularly favorable for the piston rod tip 24 to have a guide taper 48 which is blended into the front surface 50 of the piston rod tip via a small radius. The guide taper 48 reduces the shear force acting on the diaphragm 34 onto which, in accordance, pressure is exerted by the piston rod 12 merely in its central area.

The dome of the diaphragm 34 is limited by the acting of the stop 18. This means that the diaphragm 34 is never extremely stretched and can be formed with comparatively thick walls. The maximum volume of projection corresponds, for instance, to about ¹⁄₁₀ to ⅔ of the diameter of the piston rod 12, in particular to about ⅓ or ½ of the diameter of the piston rod 12.

As soon as the force acting on the piston rod 14 is removed, i.e. as soon as the actuation element 16 is released by the operator, the spring function of the diaphragm 34 takes effect. The diaphragm 34 does not only displace the piston rod 12 rearwards, i.e. in the direction towards the actuation element 16, but also enlarges the effective inner space 40 of the basic body, such that a partial vacuum is created there. As a result, in turn, dental material is taken back in through the extrusion element 46, such that a dripping out of excess material from the application device is securely prevented.

Reference it made to FIGS. 5 and 6, which show enlarged depictions of FIGS. 3 and 4, respectively. The flat front surface 50 at the front side of the piston rod tip 24 prevents any excess punctual force from being exerted on the diaphragm 34. Rather, a large-area pressure is exerted onto the diaphragm so that the dental material is squeezed out.

The taper angle of the guide taper 48 amounts to only about 30° in the exemplary embodiment depicted. It is to be understood that the guide taper angle is not limited to this angle and any angle may be realized, such as a considerably larger taper angle of, for instance, of about 120°, for even in this case it is guaranteed that the diaphragm is deformed in such a fashion that it is buckled without any excess force being exerted on it. It is also possible to combine the front surface 50 with a radius which extends to the diameter of the piston rod tip 24, but in this case it must be guaranteed that no excess load is exerted on the diaphragm 34.

The advantages and details explained with reference to FIGS. 3 to 6 are basically also applicable to the embodiments in accordance with FIGS. 1 and 2, in particular also insofar as the design of the nozzle 42 and the stretch limitation of the elastic resetting element 33 are concerned. It is to be understood that the distribution of force in the elastic resetting element 33 is even improved in the embodiment in accordance with FIGS. 1 and 2.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An application device comprising:
    a cylindrical body for storing a squeezable dental material;
    a piston positioned inside the cylindrical body and axially displaceable towards the cylindrical body;
    a piston rod serving to displace the piston in a squeezing direction, wherein the piston rod extends into the piston and is axially displaceable towards the piston;
    an elastic resetting device at a front end area of the piston and positioned in the direction towards the dental material, wherein the elastic resetting device is adaptable to be biased in the squeezing direction and to return back to a relaxed position after the end of each axial movement of the piston in the squeezing direction and release of the pressure exerted on the piston rod for this purpose, preventing dripping of excess dental material from the application device by creating a partial vacuum inside the cylindrical body, with the elastic resetting device pressing the piston rod in a direction opposite the squeezing direction;
    a stop positioned on the piston rod and facing the squeezing direction, wherein the stop is positioned at a spatial distance from the resetting device;
    wherein the bias in the resetting device is limited by the stop on the piston rod when the piston rod is actuated in the squeezing direction,
    wherein in the relaxed position of the resetting device, the piston rod contacts a contact area of the resetting device, the contact area pointing in an opposite direction to the squeezing direction, and a counterstop of the piston is positioned at a distance from the respective stop of the piston rod, the distance corresponding to the maximum bias of the resetting device,
    wherein the piston comprises the elastic resetting device and a piston body,
    wherein the elastic resetting device is a separate element from the piston body and encloses the piston body and is firmly connected to the piston body and the elastic resetting device is made of a material that is softer and more elastic than the piston body,
    wherein the elastic resetting device is never in contact with the cylindrical body.

2. The application device in accordance with claim 1, wherein the contact area of the resetting device can be biased when a squeezing force is applied by the piston rod in the squeezing direction.

3. The application device in accordance with claim 2, wherein a thickness of the wall of the resetting device is greater in the contact area.

4. The application device in accordance with claim 1, wherein the piston and the piston rod are mounted threadlessly translatory relative to each other and threadlessly axially displaceable relative to the cylindrical body, and the driving force of the piston relative to the cylindrical body is larger than the resisting force of the elastic resetting device against deformation.

5. The application device in accordance with claim 1, wherein at an outer circumference of the piston at least two sealing ribs are formed surrounding the circumference and the sealing ribs act against the cylindrical body.

6. The application device in accordance with claim 1, wherein a peripheral mounting groove or mounting shoulder is formed in the piston rod for mounting a sealing ring made out of an elastic material.

7. The application device in accordance with claim 1, wherein a peripheral mounting groove or mounting shoulder is formed in the piston for mounting a sealing ring made out of an elastic material.

8. The application device in accordance with claim 1, wherein the piston rod extends through the piston to the contact area of the resetting device, and the stop on the piston rod is formed in the elongation of the piston.

9. The application device in accordance with claim 8, wherein the stop on the piston rod is formed in the elongation of the piston at its axial center.

10. The application device in accordance with claim 1, wherein the piston comprises at least one sliding rib at its rear end, the piston supported about the piston rod in a low-friction fashion at the at least one sliding rib.

11. The application device in accordance with claim 1, further comprising an application nozzle which is attached to a surface of the cylindrical body
    pointing in the squeezing direction.

12. The application device in accordance with claim 11, wherein the cylindrical body is fillable with the application nozzle removed and the piston and the piston rod are pressed back during the filling process.

13. The application device in accordance with claim 1, wherein the piston rod comprises at least one peripheral groove which serves to mount a seal that is in contact with the inner walls of the cylindrical body.

* * * * *